United States Patent
Rampalli et al.

(10) Patent No.: US 10,435,409 B2
(45) Date of Patent: Oct. 8, 2019

(54) PROCESS FOR THE PREPARATION OF IBRUTINIB

(71) Applicant: SHILPA MEDICARE LIMITED, Raichur (IN)

(72) Inventors: Sriram Rampalli, Vizianagaram (IN); Lav Kumar Upalla, Andhra Pradesh (IN); Chanti Babu Patneedi, Andhra Pradesh (IN); Gopala Krishna Dasari, Andhra Pradesh (IN); Akshay Kant Chaturvedi, Raichur (IN)

(73) Assignee: SHILPA MEDICARE LIMITED, Raichur, Karnataka (*) Notice: Subject to any disclaimer, the term of this patent is extended or adjusted under 35 U.S.C. 154(b) by 0 days.

(21) Appl. No.: 16/073,809

(22) PCT Filed: Feb. 2, 2017

(86) PCT No.: PCT/IB2017/050553
§ 371 (c)(1),
(2) Date: Jul. 30, 2018

(87) PCT Pub. No.: WO2017/134588
PCT Pub. Date: Aug. 10, 2017

(65) Prior Publication Data
US 2019/0040069 A1    Feb. 7, 2019

(30) Foreign Application Priority Data
Feb. 4, 2016    (IN) .............................. 201641004080

(51) Int. Cl.
*C07D 487/04*    (2006.01)
*C07D 211/32*    (2006.01)

(52) U.S. Cl.
CPC .......... *C07D 487/04* (2013.01); *C07D 211/32* (2013.01)

(58) Field of Classification Search
CPC ................................................... C07D 487/04
USPC ........................................................ 544/262
See application file for complete search history.

(56) References Cited

U.S. PATENT DOCUMENTS

| 7,351,834 B1 | 4/2008 | Riedl et al. |
| 7,514,444 B2 | 4/2009 | Honigberg et al. |
| 8,637,553 B2 | 1/2014 | Boyer et al. |
| 2013/0338172 A1 | 12/2013 | Smyth et al. |

FOREIGN PATENT DOCUMENTS

| CN | 10494540 A | * | 9/2015 |
| EP | 2543375 A1 | | 1/2013 |
| WO | 2015145415 A2 | | 10/2015 |

* cited by examiner

*Primary Examiner* — Jeffrey H Murray

(57) ABSTRACT

The present invention relates to a process for the preparation of 1-[(3R)-3-[4-amino-3-(4-phenoxyphenyl)-1H-pyrazolo[3,4-d]pyrimidin-1-yl]-1-piperidinyl]-2-propen-1-one or Ibrutinib of Formula (I).

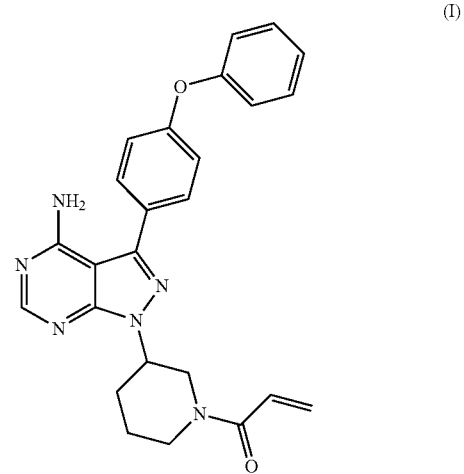

The present invention further relates to a process for the preparation highly pure 1-[(3R)-3-[4-amino-3-(4-phenoxyphenyl)-1H-pyrazolo[3,4-d]pyrimidin-1-yl]-1-piperidinyl]-2-propen-1-one or Ibrutinib(I).

5 Claims, 1 Drawing Sheet

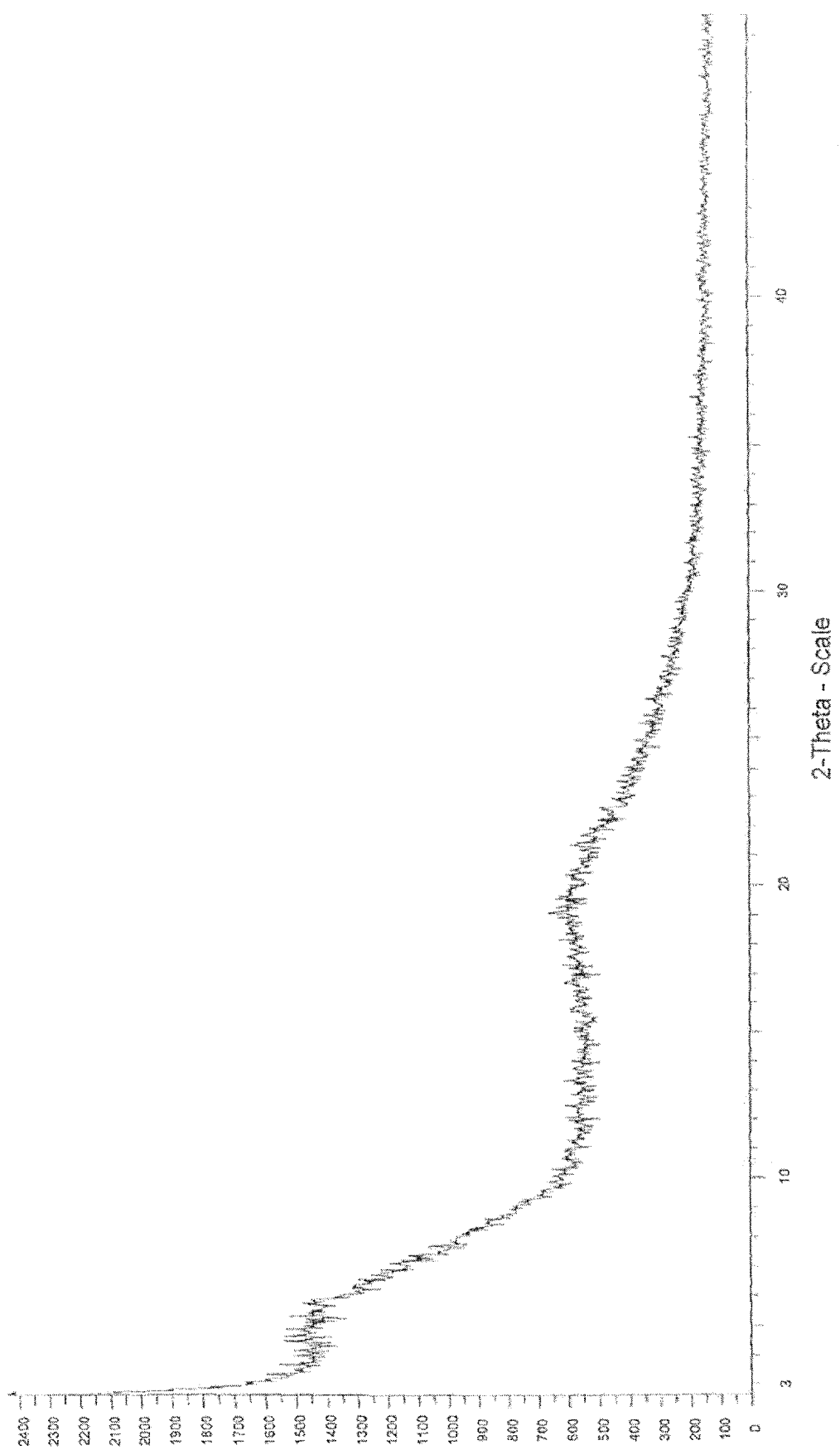

PROCESS FOR THE PREPARATION OF IBRUTINIB

FIELD OF THE INVENTION

The present invention relates to a process for the preparation of 1-[(3R)-3-[4-amino-3-(4-phenoxyphenyl)-1H-pyrazolo[3,4-d]pyrimidin-1-yl]-1-piperidinyl]-2-propen-1-one or Ibrutinib of Formula (I).

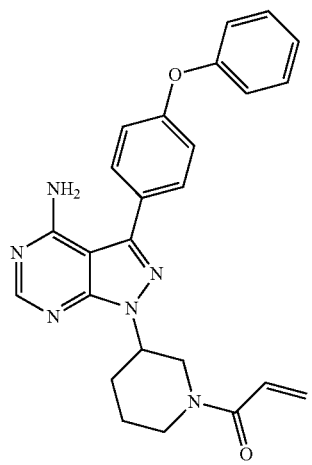

(I)

BACKGROUND OF THE INVENTION

1-[(3R)-3-[4-amino-3-(4-phenoxyphenyl)-1H-pyrazolo[3,4-d]pyrimidin-1-yl]-1-piperidinyl]-2-propen-1-one or Ibrutinibis an inhibitor of Bruton's tyrosine kinase (BTK). Ibrutinib is a small-molecule inhibitor of BTK. Ibrutinib forms a covalent bond with a cysteine residue in the BTK active site, leading to inhibition of BTK enzymatic activity. BTK is a signaling molecule of the B-cell antigen receptor (BCR) and cytokine receptor pathways. BTK's role in signaling through the B-cell surface receptors results in activation of pathways necessary for B-cell trafficking, chemotaxis, and adhesion. Nonclinical studies show that ibrutinib inhibits malignant B-cell proliferation and survival in vivo as well as cell migration and substrate adhesion in vitro.

Ibrutinib was approved by USFDA in 2013 and is marketed under the brand name IMBRUVICA®, is an important kinase inhibitor indicated for the treatment of patients with: Mantle cell lymphomas (MCL), who have received at least one prior therapy (1.1). Accelerated approval was granted for this indication based on overall response rate. Continued approval for this indication may be contingent upon verification of clinical benefit in confirmatory trials. Further, it was approved for the treatment of Chronic lymphocytic leukemia (CLL) who have received at least one prior therapy (1.2), Chronic lymphocytic leukemia with 17p deletion (1.3) and Waldenström's macroglobulinemia (WM)

Ibrutinib was chemically known as 1-[(3R)-3-[4-amino-3-(4-phenoxyphenyl)-1H-pyrazolo[3,4-d]pyrimidin-1-yl]-1-piperidinyl]-2-propen-1-one (I).

Ibrutinib is a white to off-white solid substance with the empirical formula $C_{25}H_{24}N_6O_2$ and a molecular weight of 440.5. Ibrutinib is freely soluble in dimethyl sulfoxide, soluble in methanol and practically insoluble in water.

Ibrutinib is generically disclosed in U.S. Pat. No. 7,351,834, and specifically disclosed in U.S. Pat. No. 8,637,553. These patents disclose a process for the preparation of Ibrutinib starting from 4-Aminopyrazolo[3,4-d]pyrimidine. The process is as demonstrated in Scheme-I:

Scheme-I

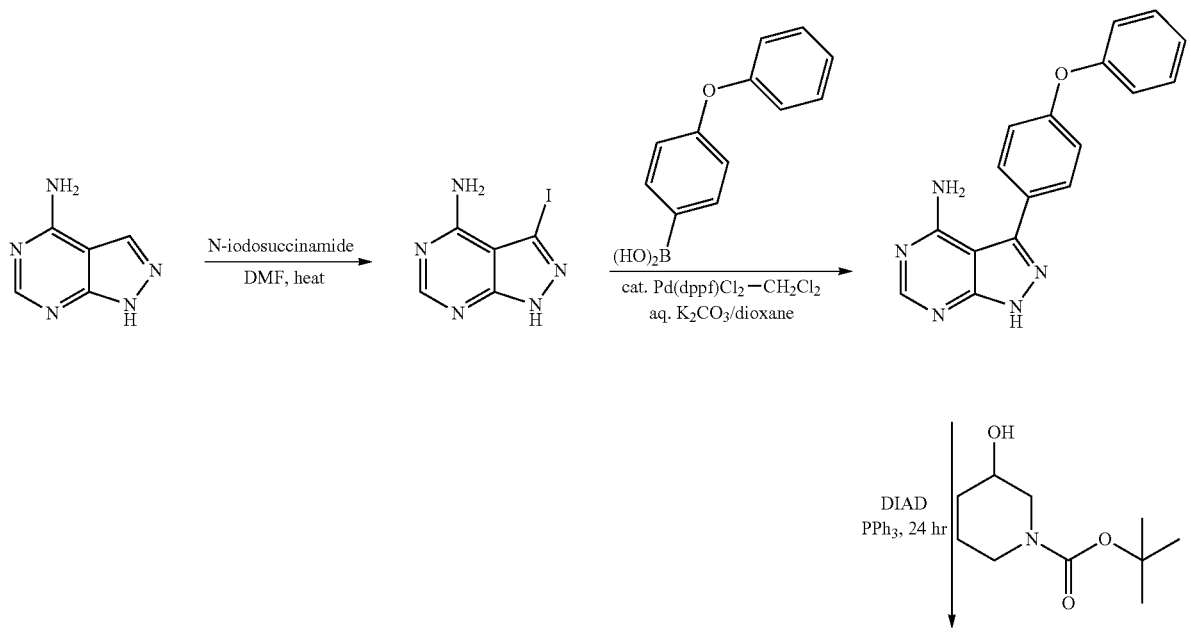

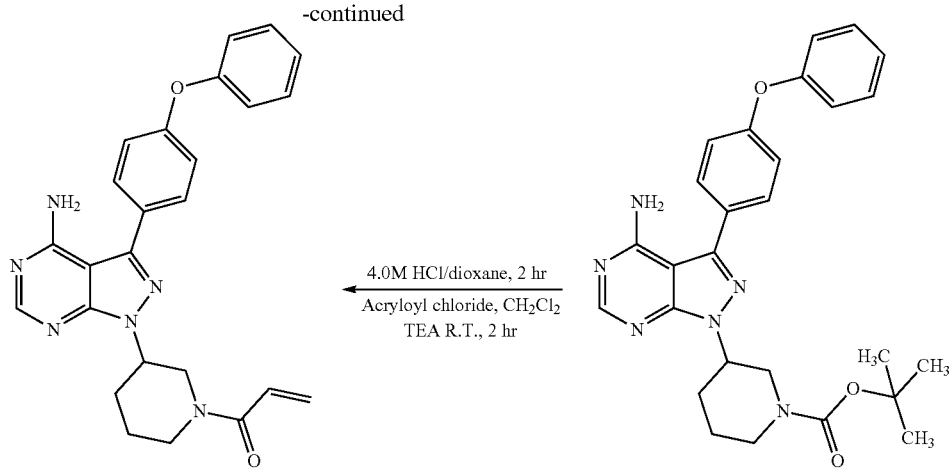

US 2013/0338172 disclose crystalline Form A, Form B, Faun C, Form D (MIBK Solvate), Form E (Toluene Solvate) and Form F (MeOH solvate) of Ibrutinib. This patent application further discloses that Ibrutinib prepared as outlined in U.S. Pat. No. 7,514,444 results in amorphous form. (Anhydrous)

EP 2543375 discloses different processes for the preparation of inhibitors of Bruton's Tyrosine Kinase. The processes disclosed in EP '375 are as disclosed below:

Scheme-II:

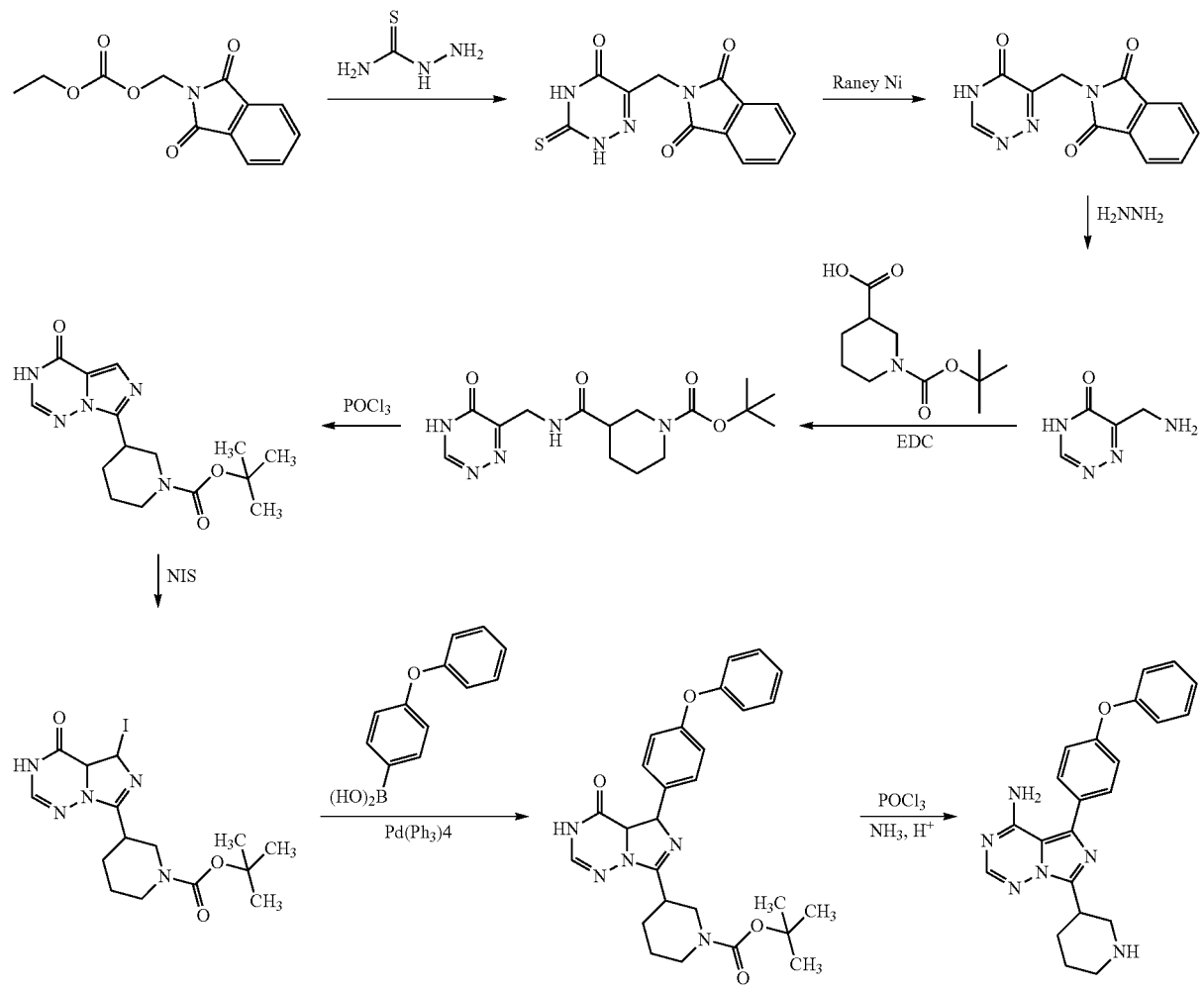

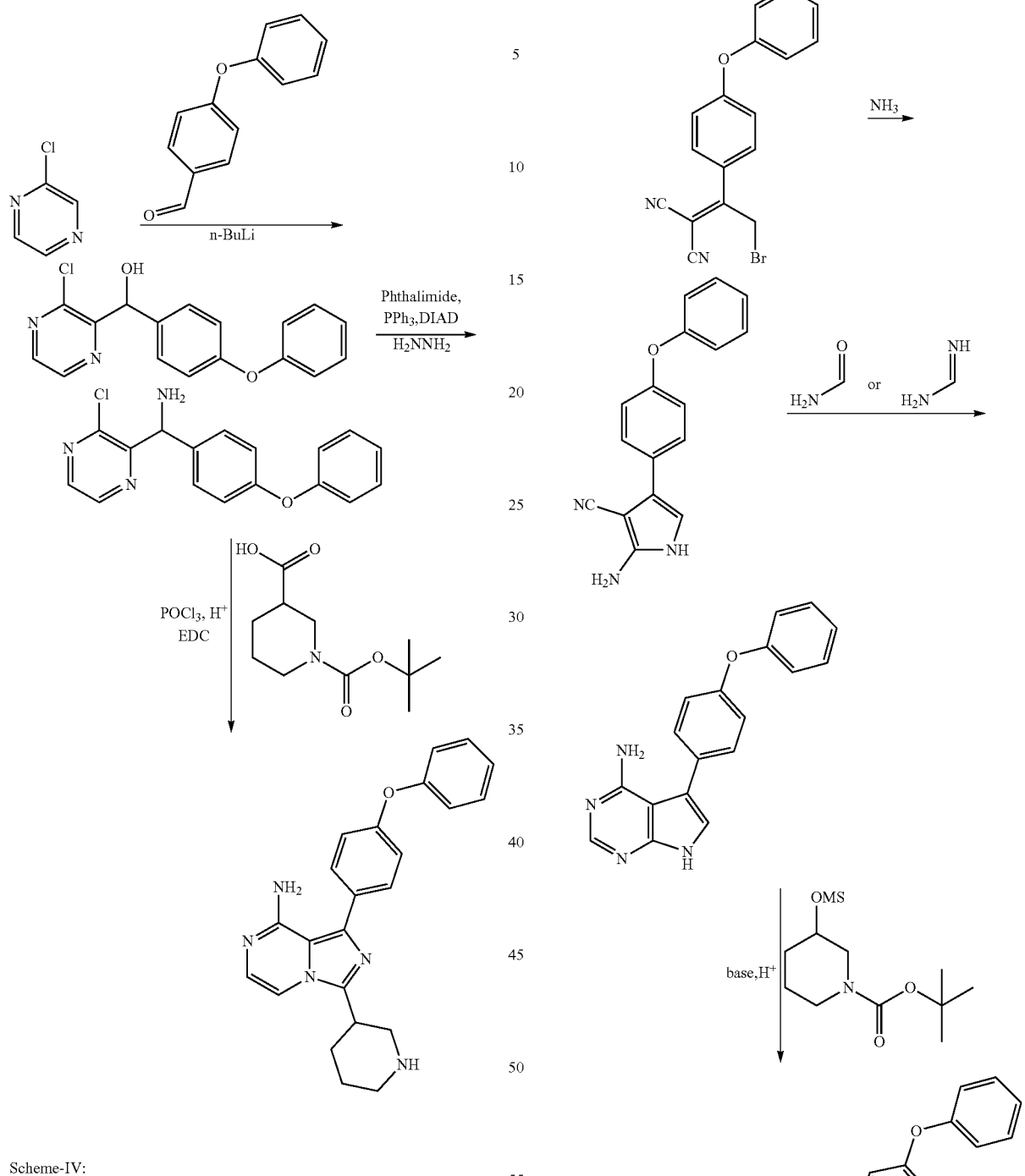
Scheme-IV:
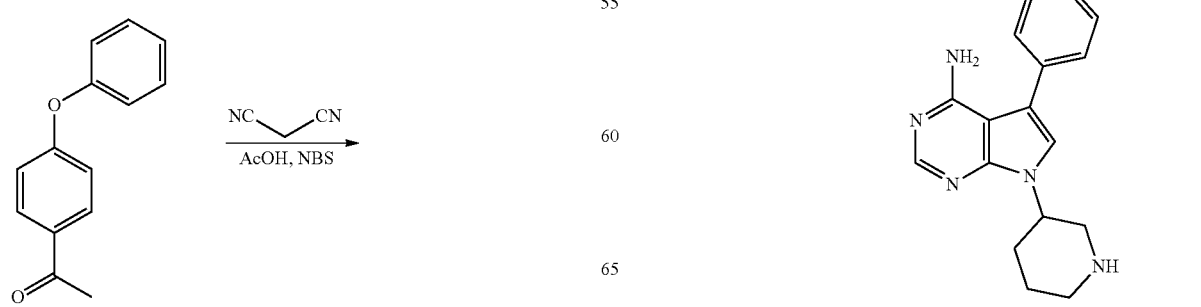

Scheme-V:
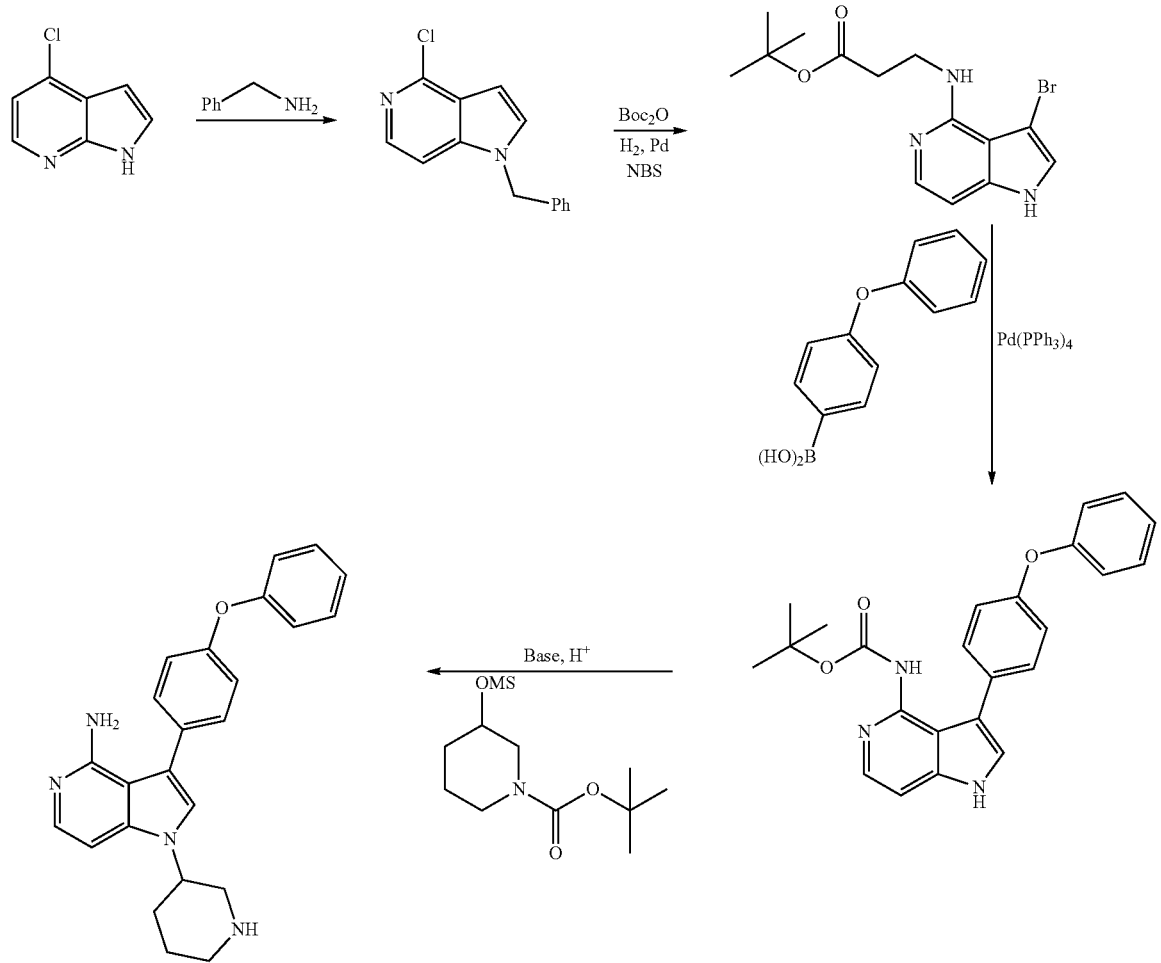
Scheme-VI:
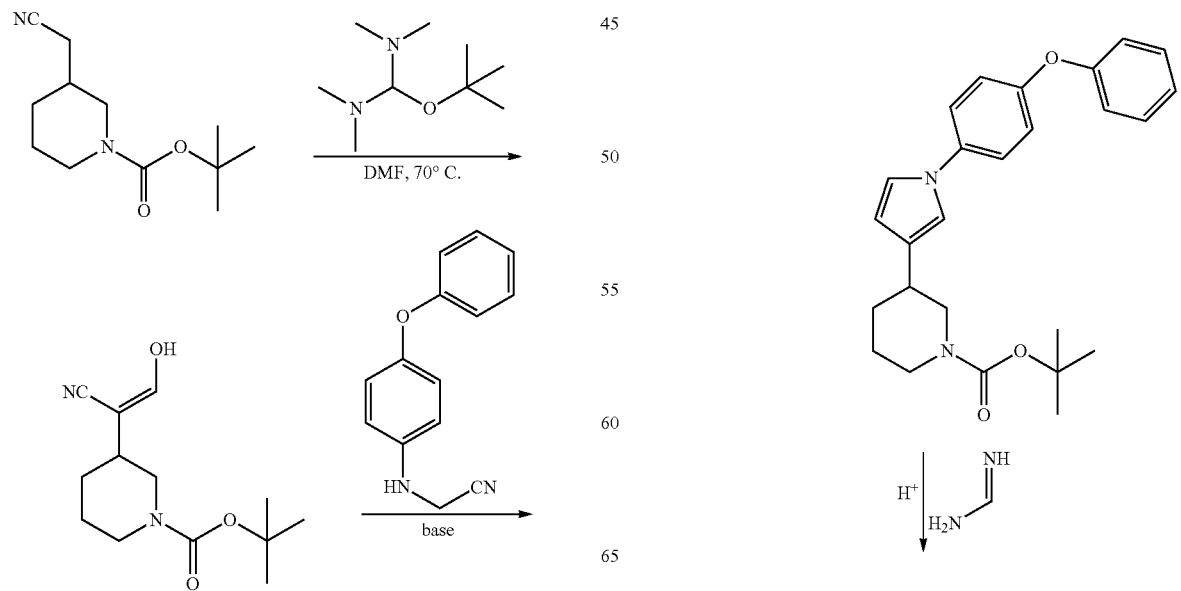

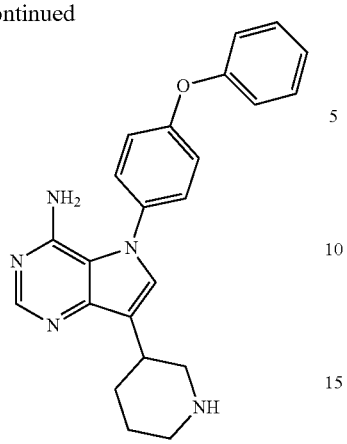

WO 2015145415 discloses crystalline Form III (1,4-dioxane solvate), Form IV(1,2-dimethoxyethane solvate), Form V (Methanol solvate), Form VI (Anhydrous), Form VII (Anisole solvate), Form VIII and Form IX (Anisole solvate) of Ibrutinib The present inventors has repeated the above process and found the following disadvantages:

- In most of the patent literature, Mitsunobu coupling was performed using costly reagents like Diazo Isopropyl Dicarboxyalate (DIAD) and Triphenyl Phosphine (TPP), which is not much efficient scalable process. Further, TPP is a Genotoxic compound, which requires several purification steps to yield highly pure Ibrutinib, which meets the requirements of ICH guidelines.
- In most of the patent literature Acryloyl chloride was used, which was easily polymerizable and not much stable compound leading to formation of majority impurities.
- Unwanted reactions are observed during the formation of Ibrutinib, due to the involvement time lagging process.
- Incomplete reactions were observed with excessive impurity formation due to incomplete conversion.

In view of the above and to overcome the prior-art problems the present inventors had now developed an improved process for the preparation of Ibrutinib, using industrially feasible and viable process, with the use of industrially friendly solvents, which does not include tedious work up and time lagging steps.

OBJECTIVE OF THE INVENTION

The main objective of the invention relates to a process for the preparation of 1-[(3R)-3-[4-amino-3-(4-phenoxyphenyl)-1H-pyrazolo[3,4-d]pyrimidin-1-yl]-1-piperidinyl]-2-propen-1-one or Ibrutinib(I).

Yet another objective of the invention relates to a process for the preparation of highly pure 1-[(3R)-3-[4-amino-3-(4-phenoxyphenyl)-1H-pyrazolo[3,4-d]pyrimidin-1-yl]-1-piperidinyl]-2-propen-1-one or Ibrutinib (I)

SUMMARY OF THE INVENTION

The present invention relates to a process for the preparation of Ibrutinib (I)

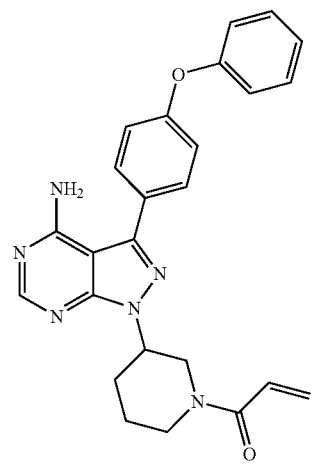

comprising the steps of:
a) reacting 3-(4-phenoxyphenyl)-1H-pyrazolo[3,4-d]pyrimidin-4-amine (II) with an activated (S)—N-protected piperidin-3-yl (III) to yield (R)-1-(1-protected piperidin-3-yl)-3-(4-phenoxyphenyl)-1H-pyrazolo[3,4-d]pyrimidin-4-amine (IV)

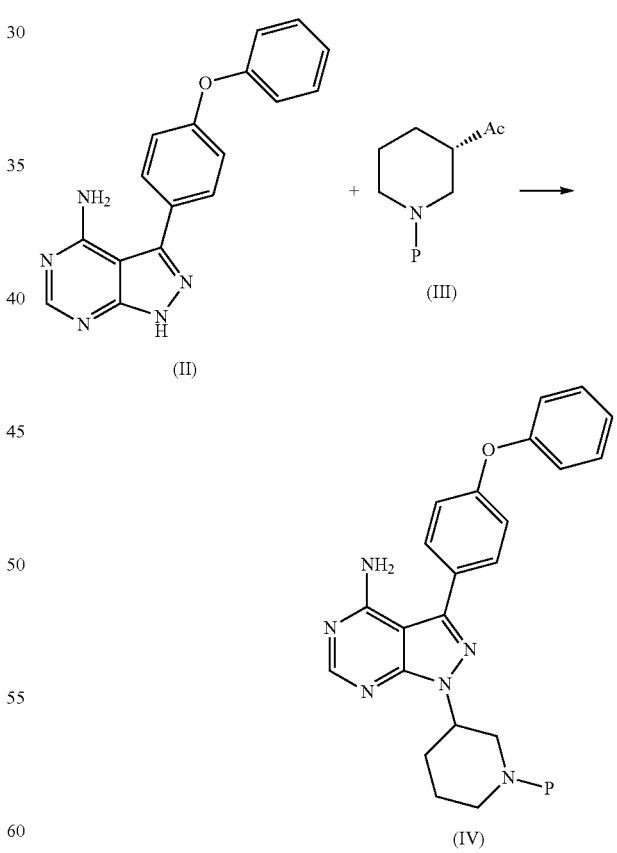

wherein Ac is activated group selected from O-Acyl, O-sulfonyl, O-Akyl, O-Aryl, orthomestylate, orthotosylate, orthobesylate; P is an amino protecting group selected from benzyl, benzoyl, acyl, tosyl, sulfonyl, trityl, carbamyl, Aryl oxy, Cbz.

b) deprotecting (R)-1-(1-protected piperidin-3-yl)-3-(4-phenoxyphenyl)-1H-pyrazolo[3,4-d]pyrimidin-4-amine (IV) to yield (R)-3-(4-phenoxyphenyl)-1-(piperidin-3-yl)-1H-pyrazolo[3,4-d]pyrimidin-4-amine (V);

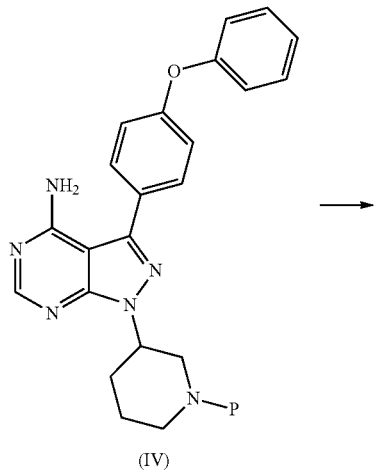

(IV)

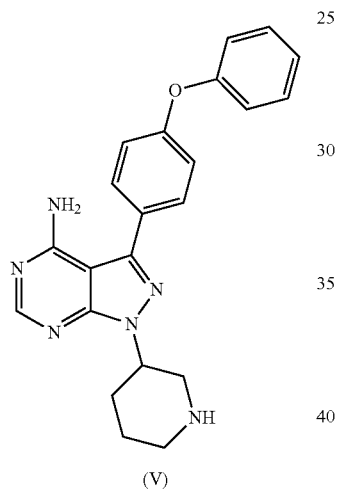

(V)

c) reacting the compound of Formula V with Acrylic acid to yield Ibrutinib

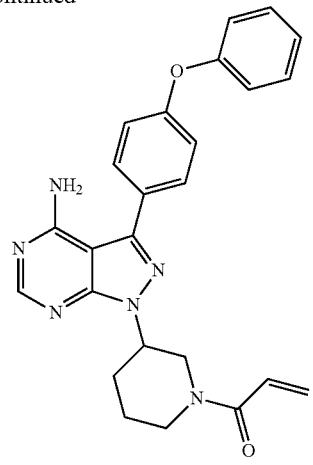

Ibrutinib

The present invention further relates to a process for the preparation of Ibrutinib (I)

(I)

comprising the steps of:

a) reacting 3-(4-phenoxyphenyl)-1H-pyrazolo[3,4-d]pyrimidin-4-amine (II) with (S)-1-benzylpiperidin-3-yl methane sulfonate (III) to yield (R)-1-(1-benzylpiperidin-3-yl)-3-(4-phenoxyphenyl)-1H-pyrazolo[3,4-d]pyrimidin-4-amine (IV)

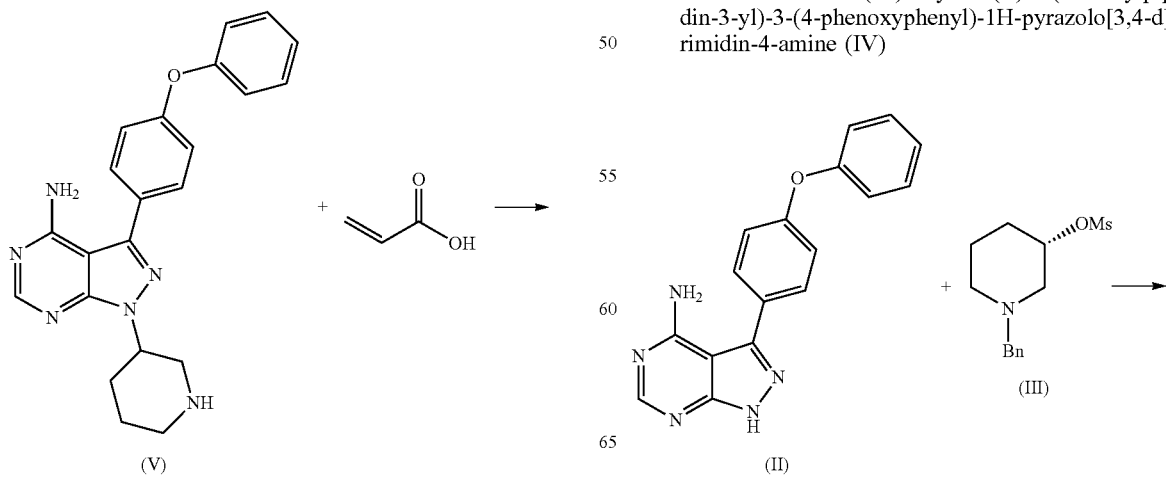

-continued

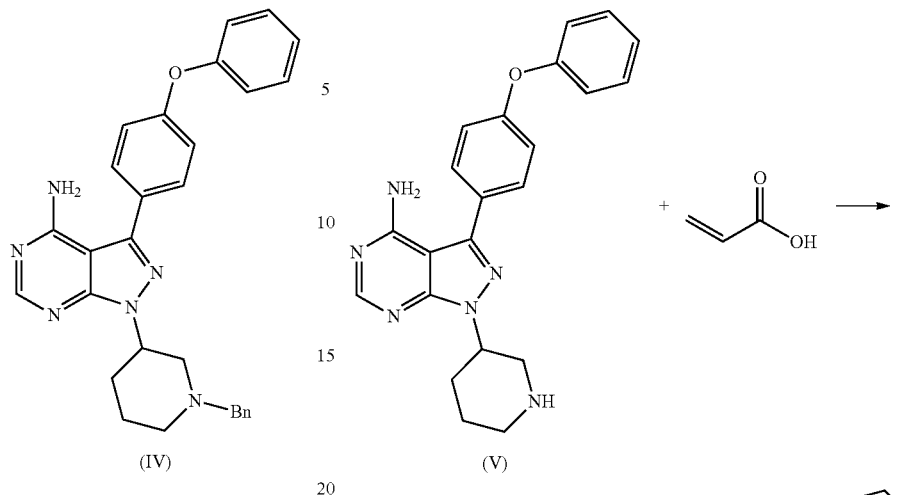

b) deprotecting (R)-1-(1-benzylpiperidin-3-yl)-3-(4-phenoxyphenyl)-1H-pyrazolo[3,4-d]pyrimidin-4-amine (IV) to yield (R)-3-(4-phenoxyphenyl)-1-(piperidin-3-yl)-1H-pyrazolo[3,4-d]pyrimidin-4-amine (V);

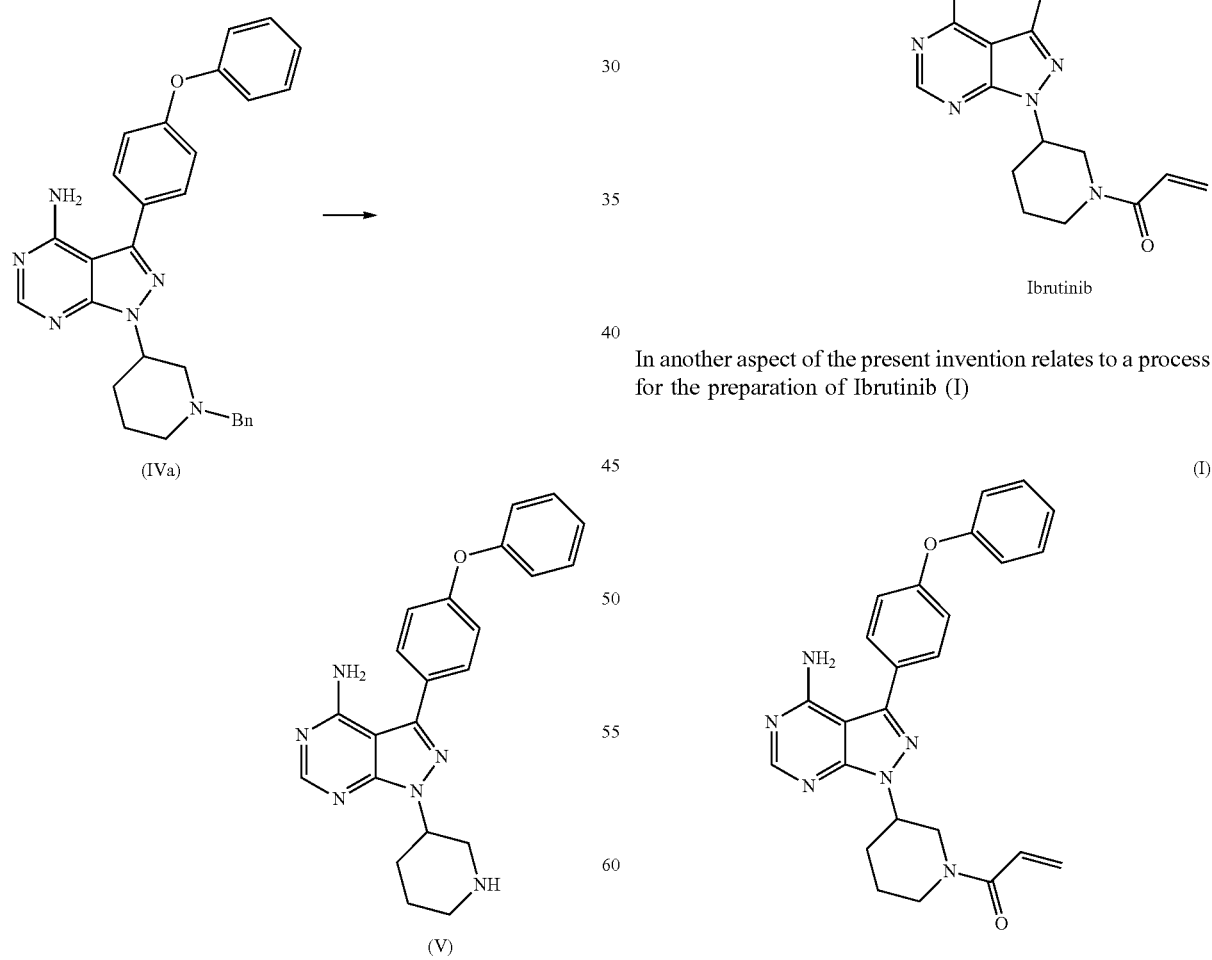

In another aspect of the present invention relates to a process for the preparation of Ibrutinib (I)

c) reacting the compound of Formula V with Acrylic acid to yield Ibrutinib comprises reacting 3-(4-phenoxyphenyl)-1H-pyrazolo[3,4-d]pyrimidin-4-amine (II) with (S)-1-acryloylpiperidin-3-yl methane sulfonate (VI) to yield Ibrutinib

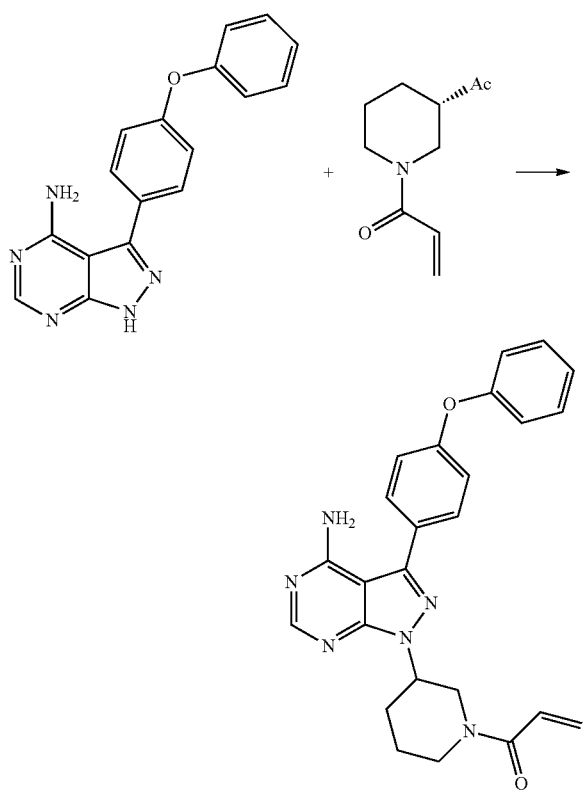

wherein Ac is activated group selected from O-Acyl, O-sulfonyl, O-Akyl, O-Aryl orthomestylate, orthotosylate, orthobesylate.

BRIEF DESCRIPTION OF THE DRAWINGS

FIG. 1 is an example of X-ray powder diffraction ("XRPD") pattern of amorphous 1-[(3R)-3-[4-amino-3-(4-phenoxyphenyl)-1H-pyrazolo[3,4-d]pyrimidin-1-yl]-1-piperidinyl]-2-propen-1-one or Ibrutinib (I) obtained according to the process of the present invention.

DETAILED DESCRIPTION OF THE INVENTION

The present invention relates to a process for the preparation of Ibrutinib (I) comprising reacting 3-(4-phenoxyphenyl)-1H-pyrazolo[3,4-d]pyrimidin-4-amine (II) with an activated (S)—N-protected piperidin-3-yl (III); wherein activated group selected from O-Acyl, O-sulfonyl, O-Akyl, O-Aryl, orthomestylate, orthotosylate, orthobesylate; P is an amino protecting group selected from benzyl, benzoyl, acyl, tosyl, Sulfonyl, Trityl, carbamyl, Aryl oxy, Cbz in an organic solvent selected from amide solvents such as formamide, dimethyl formamide, N-methyl-2-pyrrolidone, N-methyl formamide, N-vinyl acetamide, N-vinyl pyrrolidone, 2-pyrrolidone; or alcohols, such as C2-C6 alcohols like ethanol, 1-propanol, 2-propanol (isopropyl alcohol), 1-butanol, 2-butanol, t-butyl alcohol; or nitriles, such as acetonitrile or propionitrile; sulfoxides such as dimethylsulfoxide; halogenated hydrocarbons such as dichloromethane; aromatic hydrocarbons such as toluene, xylene; esters such as ethyl acetate, n-propyl acetate, n-butyl acetate, isopropyl acetate, isobutyl acetate, t-butyl acetate; ethers such as diethyl ether, diisopropyl ether, methyl t-butyl ether, tetrahydrofuran, 1,4-dioxane, 2-methoxyethanol, anisole; ketones such as acetone, ethyl methyl ketone, diethyl ketone, methyl isobutyl ketone; organic solvents such as dimethyl formamide, n-hexane, n-heptane, cyclohexane, cycloheptane; hetero aromatic solvents such as pyridine, dimethyl amino pyridine; water or mixtures thereof; and in presence of base selected from organic base such as triethylamine, methylamine, pyridine, imidazole, benzimidazole; or inorganic base selected from carbonates such as sodium carbonate, potassium carbonate, calcium carbonate, ammonium carbonate; hydroxides such as sodium hydroxide, potassium hydroxide, calcium hydroxide, ammonium hydroxide, barium hydroxide, magnesium hydroxide, lithium hydroxide, zinc hydroxide; bicarbonates such as sodium bicarbonate, potassium bicarbonate, ammonium bicarbonate, calcium bicarbonate, magnesium bicarbonate, cesium carbonate, potassium carbonate, sodium carbonate at a temperature ranging between 20-35° C. The obtained reaction mixture was heated to 40-75° C. for about 8 hours to 12 hours. Water was added and the dichloromethane layer was extracted. Purify the material by column chromatography or any of the general techniques known in the art to yield (R)-1-(1-protected piperidin-3-yl)-3-(4-phenoxyphenyl) 1H-pyrazolo[3,4-d]pyrimdin-4-amine (IV)

In an another embodiment, the above obtained (R)-1-(1-protected piperidin-3-yl)-3-(4-phenoxyphenyl)-1H-pyrazolo[3,4-d]pyrimidin-4-amine (1V) undergoes deprotectionin presence of a catalyst selected from, palladium, palladium on carbon, platinum, platinum on carbon, sodium borohydride, potassium borohydride, ammonium formate, Raney nickel, Rh and a solvent selected from alcohols, such as C2-C6 alcohols like ethanol, 1-propanol, 2-propanol (isopropyl alcohol), 1-butanol, 2-butanol, t-butyl alcohol; or nitriles, such as acetonitrile or propionitrile; amides such as N,N-dimethylformamide, N,N-dimethylacetamide, N-methyl-2-pyrrolidone; sulfoxides such as dimethylsulfoxide; halogenated hydrocarbons such as dichloromethane; aromatic hydrocarbons such as toluene, xylene; esters such as ethyl acetate, n-propyl acetate, n-butyl acetate, isopropyl acetate, isobutyl acetate, t-butyl acetate; ethers such as diethyl ether, diisopropyl ether, methyl t-butyl ether, tetrahydrofuran, 1,4-dioxane, 2-methoxyethanol, anisole; ketones such as acetone, ethyl methyl ketone, diethyl ketone, methyl isobutyl ketone; organic solvents such as dimethyl formamide, n-hexane, n-heptane, cyclohexane, cycloheptane; hetero aromatic solvents such as pyridine, dimethyl amino pyridine; water or mixtures thereof. The reaction was maintained for 8 hours to 12 hours for complete hydrogenation. Concentrate the reaction mass, the obtained residue was used for purified to yield (R)-3-(4-phenoxyphenyl)-1-(piperidin-3-yl)-1H-pyrazolo[3,4-d]pyrimidin-4-amine (V)

In an another embodiment, the above obtained (R)-3-(4-phenoxyphenyl)-1-(piperidin-3-yl)-1H-pyrazolo[3,4-d]pyrimidin-4-amine (V) was reacted with acrylic acid in presence of coupling reagent selected from 1-Ethyl-3-(3-dimethylaminopropyl)carbodimide (EDCI.HCl), DCC, HOBt, HAUL TATU, CDI or in combination thereof and in presence of base was added, which was selected from organic base such as triethylamine, methylamine, pyridine, imidazole, benzimidazole; or inorganic base selected from carbonates such as sodium carbonate, potassium carbonate, calcium carbonate, ammonium carbonate; hydroxides such as sodium hydroxide, potassium hydroxide, calcium hydroxide, ammonium hydroxide, barium hydroxide, magnesium hydroxide, lithium hydroxide, zinc hydroxide; bicarbonates such as sodium bicarbonate, potassium bicarbonate, ammonium bicarbonate, calcium bicarbonate, magnesium bicarbonate; at a temperature ranging from 10-30° C. for a period of 2 hours to 6 hours to yield Ibrutinib.

In an another embodiment of the present invention provides a process for the preparation of 1-[(3R)-3-[4-amino-3-(4-phenoxyphenyl)-1H-pyrazolo[3,4-d]pyrimidin-1-yl]-1-piperidinyl]-2-propen-1-one or Ibrutinib (I) comprising 3-(4-phenoxyphenyl)-1H-pyrazolo[3,4-d]pyrimidin-4- amine with (S)-1-benzylpiperidin-3-yl methane sulfonate in an solvent selected from alcohols, such as C2-C6 alcohols like ethanol, 1-propanol, 2-propanol (isopropyl alcohol), 1-butanol, 2-butanol, t-butyl alcohol; or nitriles, such as acetonitrile or propionitrile; amides such as N,N-dimethylformamide, N,N-dimethylacetamide, N-methyl-2-pyrrolidone; sulfoxides such as dimethylsulfoxide; halogenated hydrocarbons such as dichloromethane; aromatic hydrocarbons such as toluene, xylene; esters such as ethyl acetate, n-propyl acetate, n-butyl acetate, isopropyl acetate, isobutyl acetate, t-butyl acetate; ethers such as diethyl ether, diisopropyl ether, methyl t-butyl ether, tetrahydrofuran, 1,4-dioxane, 2-methoxyethanol, anisole; ketones such as acetone, ethyl methyl ketone, diethyl ketone, methyl isobutyl ketone; organic solvents such as dimethyl formamide, n-hexane, n-heptane, cyclohexane, cycloheptane; hetero aromatic solvents such as pyridine, dimethyl amino pyridine; water or mixtures thereof; and in presence of base, which was selected from organic base such as triethylamine, methylamine, pyridine, imidazole, benzimidazole; or inorganic base selected from carbonates such as sodium carbonate, potassium carbonate, calcium carbonate, ammonium carbonate; hydroxides such as sodium hydroxide, potassium hydroxide, calcium hydroxide, ammonium hydroxide, barium hydroxide, magnesium hydroxide, lithium hydroxide, zinc hydroxide; bicarbonates such as sodium bicarbonate, potassium bicarbonate, ammonium bicarbonate, calcium bicarbonate, magnesium bicarbonate, cesium carbonate, potassium carbonate, sodium carbonate; at a temperature ranging between 20-35° C. The obtained reaction mixture was heated to 40-75° C. for about 8 hours to 12 hours. Water was added and the dichloromethane layer was extracted. Purify the material by column chromatography using dichloromethane and methanol solvent system to obtain (R)-1-(1-benzylpiperidin-3-yl)-3-(4-phenoxyphenyl)-1H-pyrazolo[3,4-d]pyrimidin-4-amine.

In one embodiment, the present inventors surprisingly found that use of an activated (S)-1-benzylpiperidine leads to provide (R)-1-(1-benzylpiperidin-3-yl)-3-(4-phenoxyphenyl)-1H-pyrazolo[3,4-d]pyrimidin-4-amine in higher yields compare to the prior-art process. Further, the present inventors found that the use of activated (S)-1-benzylpiperidine, wherein activated by O-Acyl, O-sulfonyl, O-Akyl, O-Aryl, orthomestylate, orthotosylate, orthobesylate; and the compounds like yields not only in the formation of highly pure (R)-1-(1-benzylpiperidin-3-yl)-3-(4-phenoxyphenyl)-1H-pyrazolo[3,4-d]pyrimidin-4-amine but also leads in the formation of highly pure (R)-1-(1-benzylpiperidin-3-yl)-3-(4-phenoxyphenyl)-1H-pyrazolo[3,4-d]pyrimidin-4-amine free of genotoxic impurity.

The present inventors found that use of N-protected (S) 3-Hydroxy piperidine, wherein —N is protected using benzyl, benzoyl, acyl, tosyl, sulfonyl, trityl, carbamyl, Aryl oxy, Cbz as a protecting groups was cost effective than N-Boc (S) 3-Hydroxy piperidine.

On the other hand, the prior art processes involves the use of Genotoxic reagents like TPP, involves continuous purifications to yield an intermediate meting the ICH guidelines, which parallel lowering the quantity of yield. The present inventors also found that the use of N-boc protected also leads in the conversion of reactant in the range of 30-35% only, which means that the reaction becomes incomplete.

In another embodiment, the present inventors surprisingly found that the use of activated intermediates and in combination with protected groups is advantageous over prior art, as the reaction completes within hours and conversion is also greater than 95%.

Further, use of these novel intermediates completes the reaction within hours also helps in avoiding the unwanted reactions and minimizes the formation of impurity in the formation (R)-1-(1-benzylpiperidin-3-yl)-3-(4-phenoxyphenyl)-1H-pyrazolo[3,4-d]pyrimidin-4-amine (R)-1-(1-benzylpiperidin-3-yl)-3-(4-phenoxyphenyl)-1H-pyrazolo[3,4-d]pyrimidin-4-amine was added slowly over a period of 5 to 10 minutes under nitrogen gas in to a reaction flask containing a solvent selected from alcohols, such as C2-C6 alcohols like ethanol, 1-propanol, 2-propanol (isopropyl alcohol), 1-butanol, 2-butanol, t-butyl alcohol; or nitriles, such as acetonitrile or propionitrile; amides such as N,N-dimethylformamide, N,N-dimethylacetamide, N-methyl-2-pyrrolidone; sulfoxides such as dimethylsulfoxide; halogenated hydrocarbons such as dichloromethane; aromatic hydrocarbons such as toluene, xylene; esters such as ethyl acetate, n-propyl acetate, n-butyl acetate, isopropyl acetate, isobutyl acetate, t-butyl acetate; ethers such as diethyl ether, diisopropyl ether, methyl t-butyl ether, tetrahydrofuran, 1,4-dioxane, 2-methoxyethanol, anisole; ketones such as acetone, ethyl methyl ketone, diethyl ketone, methyl isobutyl ketone; organic solvents such as dimethyl formamide, n-hexane, n-heptane, cyclohexane, cycloheptane; hetero aromatic solvents such as pyridine, dimethyl amino pyridine; water or mixtures thereof. To the solution deprotecting catalyst selected from, palladium, palladium on carbon, platinum, platinum on carbon, sodium borohydride, potassium borohydride, ammonium formate, Raney nickel, Rh was added. The reaction was maintained for 8 hours to 12 hours for complete hydrogenation. Concentrate the reaction mass, the obtained residue was used for further process without purification.

The present inventors found that the removal of protecting groups such as benzyl, benzoyl, acyl, tosyl, sulfonyl, trityl, carbamyl, Aryl oxy, Cbz as a protecting groups was not only cost effective than N-Boc deprotection and was simple, efficient and does not yield any additional impurities.

(R)-3-(4-phenoxyphenyl)-1-(piperidin-3-yl)-1H-pyrazolo[3,4-d]pyrimidin-4-amine obtained above was reacted with acrylic acid in presence of coupling reagent selected from 1-Ethyl-3-(3-dimethylaminopropyl)carbodiimide (EDCI), DCC, HOBt, HATU, TATU, CDI or in combination thereof and in presence of base selected from inorganic/organic base such as sodium hydroxide, potassium hydroxide, calcium hydroxide, sodium carbonate, potassium carbonates, sodium bi carbonate, potassium bicarbonate, triethyl amine, ammonia, pyridine, methyl amine, imidazole, benziimidazole; at a temperature raging from 10-30° C. for a period of 2 hours to 6 hours to yield Ibrutinib.

In another embodiment the present invention relates to a process for the preparation of Ibrutinib (1) comprises reacting 3-(4-phenoxyphenyl)-1H-pyrazolo[3,4-d]pyrimidin-4-amine (II) with activated (S)-1-acryloylpiperidin-3-yl (VI), wherein Ac is activated group selected from O-Acyl, O-sulfonyl, O-Akyl, O-Aryl, orthomestylate, orthotosylate, orthobesylate in presence of solvent selected from organic solvent such as solvent selected from alcohols, such as C2-C6 alcohols like ethanol, 1-propanol, 2-propanol (isopropyl alcohol), 1-butanol, 2-butanol, t-butyl alcohol; or nitriles, such as acetonitrile or propionitrile; amides such as N,N-dimethylformamide, N,N-dimethylacetamide, N-methyl-2-pyrrolidone; sulfoxides such as dimethylsulfoxide; halogenated hydrocarbons such as dichloromethane; aromatic hydrocarbons such as toluene, xylene; esters such as ethyl acetate, n-propyl acetate, n-butyl acetate, isopropyl acetate, isobutyl acetate, t-butyl acetate; ethers such as diethyl ether, diisopropyl ether, methyl t-butyl ether, tetrahydrofuran, 1,4-dioxane, 2-methoxyethanol, anisole; ketones such as acetone, ethyl methyl ketone, diethyl ketone, methyl isobutyl ketone; organic solvents such as formamide, dimethyl formamide, N-methyl-2-pyrrolidone, N-methyl formamide, N-vinyl acetamide, N-vinyl pyrrolidone, 2-pyrrolidone, n-hexane, n-heptane, cyclohexane, cycloheptane; hetero aromatic solvents such as pyridine, dimethyl amino pyridine; water or mixtures thereof; and a base selected from organic base such as triethylamine, diisopropyl ethyl amine, methylamine, pyridine, imidazole, benzimidazole; or inorganic base selected from carbonates such as sodium carbonate, potassium carbonate, calcium carbonate, ammonium carbonate; hydroxides such as sodium hydroxide, potassium hydroxide, calcium hydroxide, ammonium hydroxide, barium hydroxide, magnesium hydroxide, lithium hydroxide, zinc hydroxide; bicarbonates such as sodium bicarbonate, potassium bicarbonate, ammonium bicarbonate, calcium bicarbonate, magnesium bicarbonate, cesium carbonate, potassium carbonate, sodium carbonate at a temperature ranging from 45-150° C. for an about 4-6 hrs to yield Ibrutinib.

The obtained Ibrutinib was purified using a polar solvent selected from selected from ketone solvents such as acetone, methyl ethyl ketone, methyl isopropyl ketone, methyl isobutyl ketone (MIBK); amide solvents such as formamide, dimethyl formamide, N-methyl-2-pyrrolidone, N-methyl formamide, N-vinylacetamide, N-vinyl pyrrolidone, 2-pyrrolidone; alcohols, such as methanol, ethanol, isopropanol; ethers such as tetrahydrofuran, dioxane; water or mixtures thereof or a mixture of polar and hydrocarbon solvent selected from selected from toluene, xylene, cyclohexane, hexane; halogenated hydrocarbons such as methylene dichloride, ethylene chloride, chloroform; or mixtures thereof; at a temperature ranging from 60-110° C., by stirring the reaction mixture for 15 to 45 minutes, cooling to room temperature and continued stirring for 30 minutes to 2 hours; the obtained reaction mixture was filtered and washed with polar non-polar solvent to yield pure Ibrutinib. The obtained Ibrutinib was purified using column chromatography using polar/non-polar solvents to yield pure Ibrutinib.

Drying may be also be performed by any conventional process not limited to spray drying or distillation to remove the solvent. Drying may be performed under reduced pressure conditions also. Reduced pressure conditions may be suitably utilized by person skilled in the art in order to obtain the dried material. The drying may be performed at a temperature ranging from 50-65° C. for a time ranging from 12 to 16 hours depending upon the physical attributes of the end product obtained i.e. Pure Ibrutinib. 1-((3R)-3-(4-amino-3-(4-phenoxyphenyl)-1H-pyrazolo[3,4-d]pyrimidin-1-yl)cyclohexyl)prop-2-en-1-one (1) or Ibrtuinib obtained according to the present invention is having purity greater than 99.5%.

The obtained pure 1-((3R)-3-(4-amino-3-(4-phenoxyphenyl)-1H-pyrazolo[3,4-d]pyrimidin-1-yl)cyclohexyl)prop-2-en-1-one (I) or Ibrutinib having purity greater than 99.5% and substantially free from process related impurities and meets the requirement of ICH guidelines.

Ibrutinib obtained according to the present invention is having purity of greater than 99.5% and substantially free from process related impurities. Ibrutinib obtained according to the present invention is analyzed by PXRD and obtained PXRD pattern appears to be amorphous.

The process related impurities that appear in the impurity profile of the 41-((3R)-3-(4-amino-3-(4-phenoxyphenyl)-1H-pyrazolo[3,4-d]pyrimidin-1-yl)cyclohexyl)prop-2-en-1-one (I) or Ibrutinib may be substantially removed by the process of the present invention resulting in the formation of highly pure material. The process of the present invention is as summarized below:

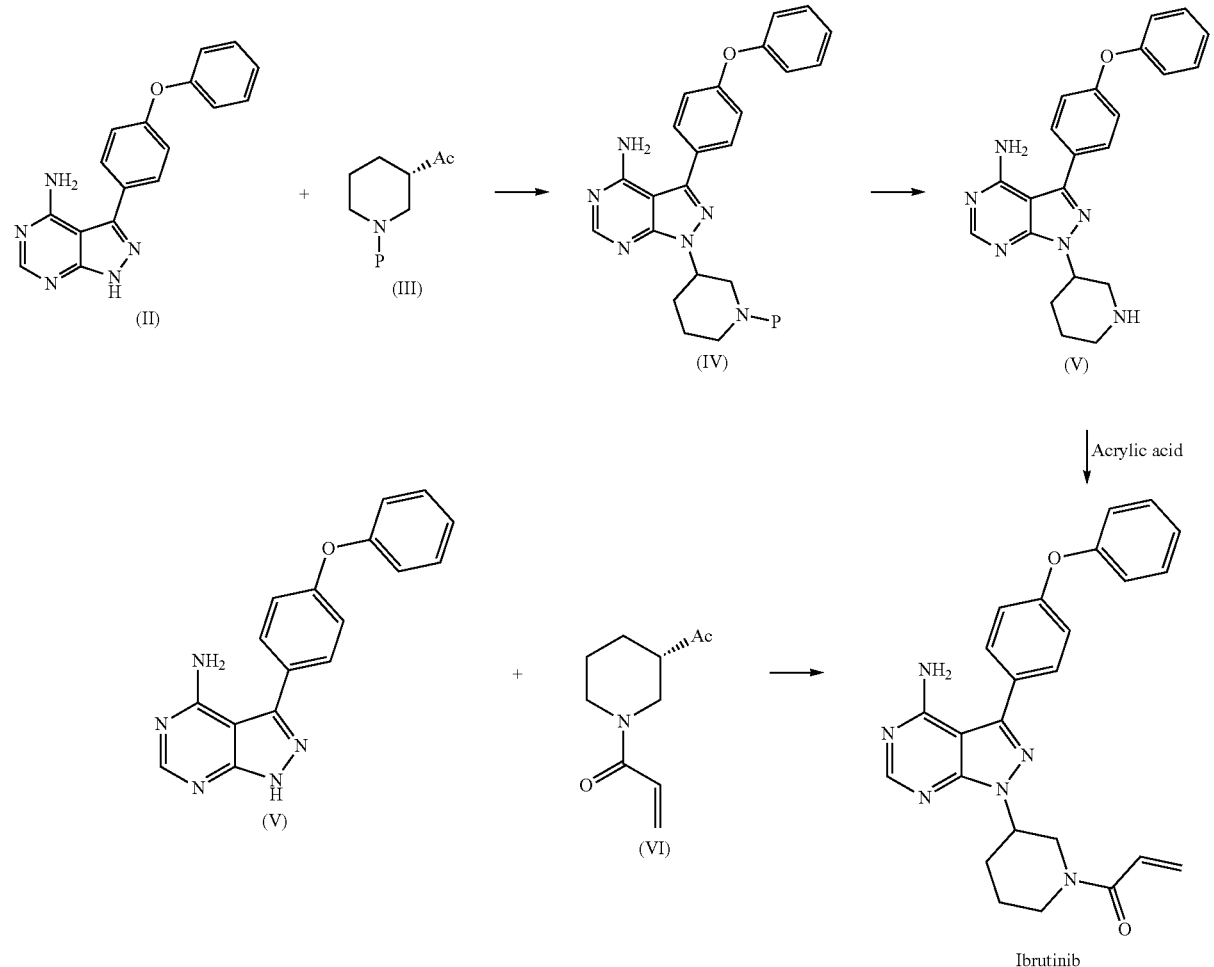

In another embodiment the present invention relates to a novel intermediate of Formula (IV) useful in the synthesis of Ibrutinib

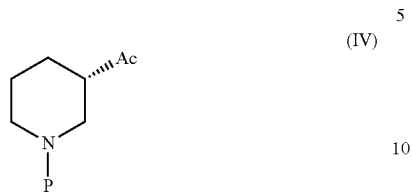

(IV)

In another embodiment of the present invention relates to a process for the preparation of novel intermediate of Formula (IV)

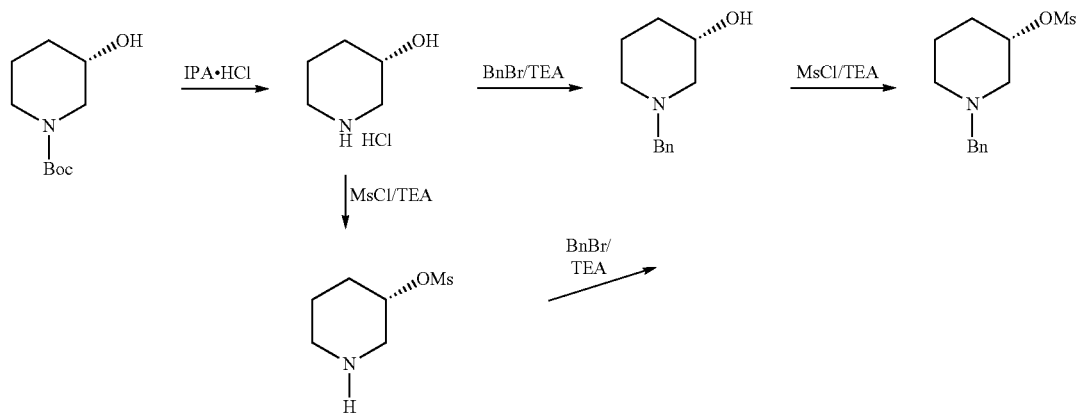

In another embodiment the present invention relates to a novel intermediate of Formula (VI) useful in the synthesis of Ibrutinib

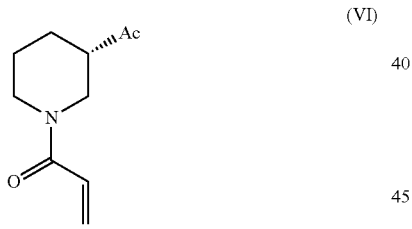

(VI)

In another embodiment of the present invention relates to a process for the preparation of novel intermediate of Formula (VI)

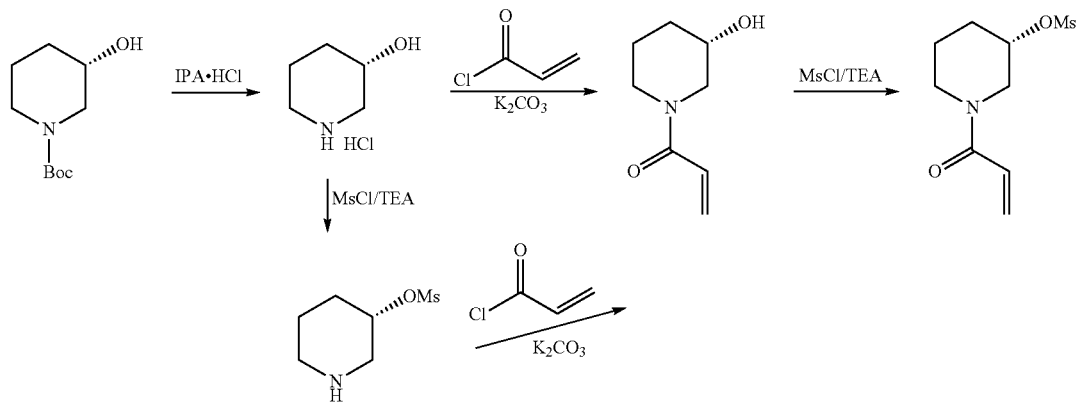

In another embodiment, the 1-((3R)-3-(4-amino-3-(4-phenoxyphenyl)-1H-pyrazolo[3,4-d]pyrimidin-1-yl)cyclohexyl)prop-2-en-1-one (I) or Ibrutinib obtained by the processes of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerine, propylene glycol or liquid paraffin.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters. e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising 1-((3R)-3-(4-amino-3-(4-phenoxyphenyl)-1H-pyrazolo[3,4-d]pyrimidin-1-yl)cyclohexyl)prop-2-en-1-one (I) or Ibrutinib obtained as per the present application process—include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from 1-((3R)-3-(4-amino-3-(4-phenoxyphenyl)-1H-pyrazolo[3,4-d]pyrimidin-1-yl)cyclohexyl) prop-2-en-1-one (I) or Ibrutinib of the present application may also comprise to include the pharmaceutically acceptable carrier used for the preparation of solid dispersion, wherever utilized in the desired dosage form preparation.

The following examples illustrate the nature of the invention and are provided for illustrative purposes only and should not be construed to limit the scope of the invention.

EXAMPLES

Example 1

Preparation of (R)-1-(1-benzylpiperidin-3-yl)-3-(4-phenoxyphenyl)-1H-pyrazolo[3,4-d]pyrimidin-4-amine In a 100 mL single neck RBF charged DMF (10 v) 50 mL, 3-(4-phenoxyphenyl)-1H-pyrazolo[3,4-d]pyrimidin-4-amine 5.0 g (1.0 Eq), (S)-1-benzylpiperidin-3-yl methane sulfonate (1.5 Eq) 6.6 g and Cesium carbonate (2.0 Eq) 10.75 g at 25-30° C. Heat the reaction mass to 55-60° C. for about 10-12 hrs, charge water and extract with DCM. Purify the material by column chromatography using DCM: Methanol solvent system.

Yield: 5.5 gm

Example 2

Preparation of (R)-3-(4-phenoxyphenyl)-1-(piperidin-3-yl)-1H-pyrazolo[3,4-d]pyrimidin-4-amine In a 100 mL RBF charge Methanol (10 v) 50 mL and (R)-1-(1-benzylpiperidin-3-yl)-3-(4-phenoxyphenyl)-1H-pyrazolo[3,4-d]pyrimidin-4-amine 5.0 g, purge the reaction mass with Nitrogen gas. Charge 10% Palladium on carbon (50% wet) 1.0 g and purge the reaction mass with Nitrogen gas. Maintain the reaction mass under stirring with Hydrogen pressure for about 10-12 hrs. Concentrate reaction mass, obtained residue was used for further process without purification.

Yield: 4.0 gm

Example 3

Preparation of 1-((3R)-3-(4-amino-3-(4-phenoxyphenyl)-1H-pyrazolo[3,4-d]pyrimidin-1-yl)cyclohexyl)prop-2-en-1-one (IBRUTINIB)

In a 100 mL RBF charge DCM (20 v) 80 mL, (R)-3-(4-phenoxyphenyl)-1-(piperidin-3-yl)-1H-pyrazolo[3,4-d]pyrimidin-4-amine (1.0 Eq) 4.0 g, 1-Ethyl-3-(3-dimethylaminopropyl)carbodimide (EDCI.HCl) (2.0 Eq) 4.0 g, Acrylic acid (2.5 Eq) 1.86 g and Triethyl amine (8.0 Eq) 8.37 g at10-30° C. Maintain the reaction for about 3-5 hrs and then charge water and work up with DCM, acidic and basic wash the organic layer. Concentrate and purify by column chromatography using DCM: Methanol solvent system.

Yield: 2.0 gm

Example 4

Preparation of 1-((3R)-3-(4-amino-3-(4-phenoxyphenyl)-1H-pyrazolo[3,4-d]pyrimidin-1-yl)cyclohexyl)prop-2-en-1-one (IBRUTINIB)

In a 100 mL single neck RBF charged DMF(10 v) 40 mL, 3-(4-phenoxyphenyl)-1H-pyrazolo[3,4-d]pyrimidin-4-amine 4.0 g, (S)-1-acryloylpiperidin-3-yl methane sulfonate (1.5 Eq) 4.6 g, and Cesium carbonate (2 Eq) 8.6 g at 25-30° C. Heat the reaction mass to 55-60° C. for about 6 hrs, charge water and extract with Ethyl acetate. Purify the material by column chromatography using DCM:Methanol solvent system.

Yield: 3.0 gm

While the foregoing pages provide a detailed description of the preferred embodiments of the invention, it is to be understood that the description and examples are illustrative only of the principles of the invention and not limiting. Furthermore, as many changes can be made to the invention without departing from the scope of the invention, it is intended that all material contained herein be interpreted as illustrative of the invention and not in a limiting sense.

The invention claimed is:

1. A process for the preparation of Ibrutinib (I)

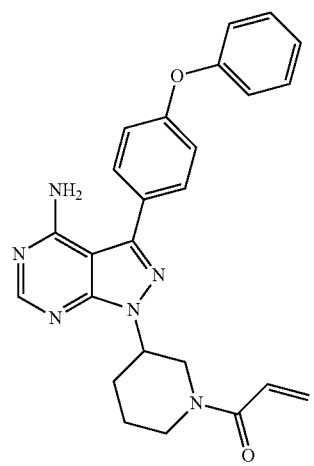
(I)

comprising the steps of:

a) reacting 3-(4-phenoxyphenyl)-1H-pyrazolo[3,4-d]pyrimidin-4-amine (II) with an activated (S)—N-protected piperidin-3-yl (III) to yield (R)-1-(1-protected piperidin-3-yl)-3-(4-phenoxyphenyl)-1H-pyrazolo[3,4-d]pyrimidin-4-amine (IV)

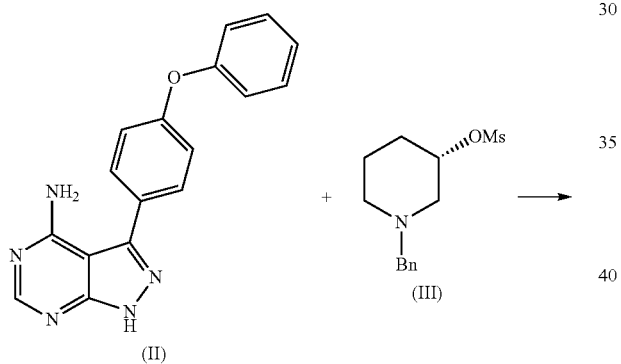

b) deprotecting (R)-1-(1-protected piperidin-3-yl)-3-(4-phenoxyphenyl)-1H-pyrazolo[3,4-d]pyrimidin-4-amine (IV) to yield (R)-3-(4-phenoxyphenyl)-1-(piperidin-3-yl)-1H-pyrazolo[3,4-d]pyrimidin-4-amine (V);

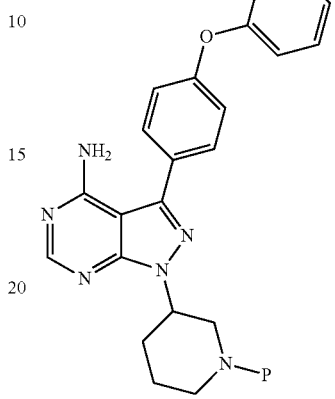
(IV)

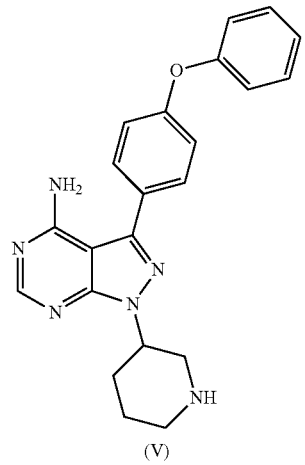
(V)

c) reacting the compound of Formula V with Acrylic acid to yield Ibrutinib

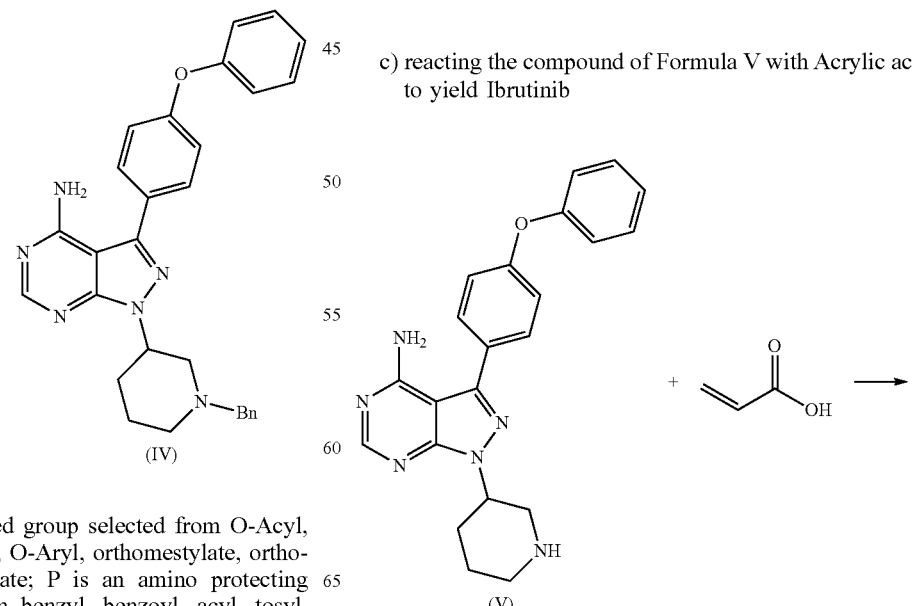

wherein Ac is activated group selected from O-Acyl, O-sulfonyl, O-Akyl, O-Aryl, orthomestylate, orthotosylate, orthobesylate; P is an amino protecting group selected from benzyl, benzoyl, acyl, tosyl, sulfonyl, trityl, carbamyl, Aryl oxy, Cbz, -continued

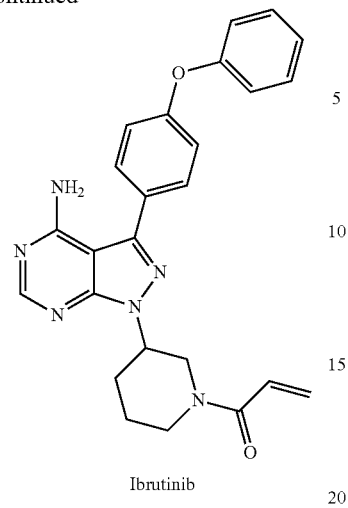

Ibrutinib

2. A process for the preparation of Ibrutinib (I)

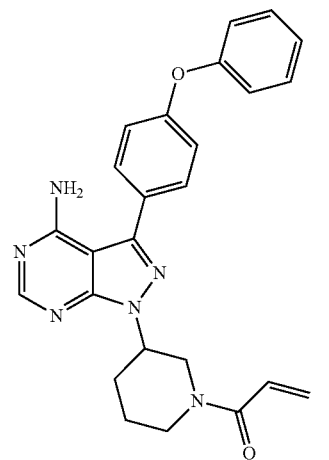

(I)

comprising the steps of:

a) reacting 3-(4-phenoxyphenyl)-1H-pyrazolo[3,4-d]pyrimidin-4-amine (II) with (S)-1-benzylpiperidin-3-yl methane sulfonate (IIIa) to yield (R)-1-(1-benzylpiperidin-3-yl)-3-(4-phenoxyphenyl)-1H-pyrazolo[3,4-d]pyrimidin-4-amine (IVa)

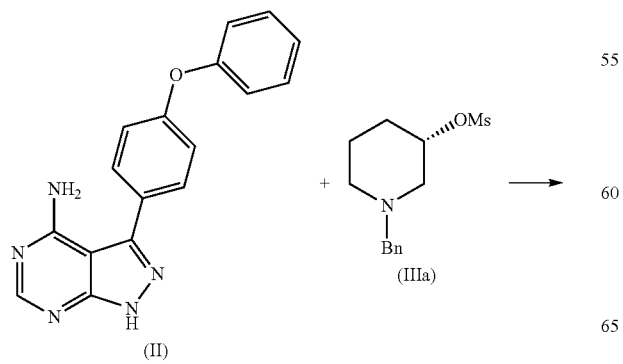

-continued

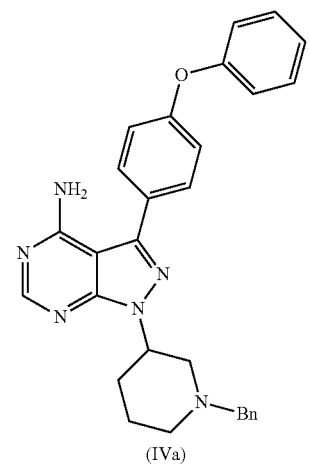

(IVa)

b) deprotecting (R)-1-(1-benzylpiperidin-3-yl)-3-(4-phenoxyphenyl)-1H-pyrazolo[3,4-d]pyrimidin-4-amine (IVa) to yield (R)-3-(4-phenoxyphenyl)-1-(piperidin-3-yl)-1H-pyrazolo[3,4-d]pyrimidin-4-amine (V);

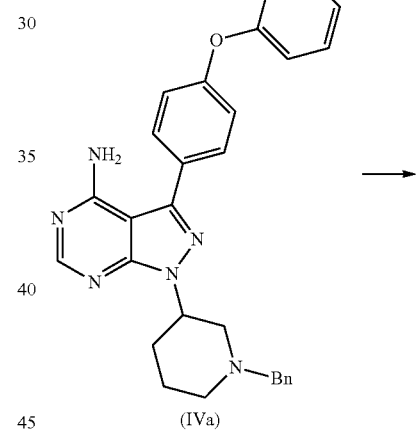

(IVa)

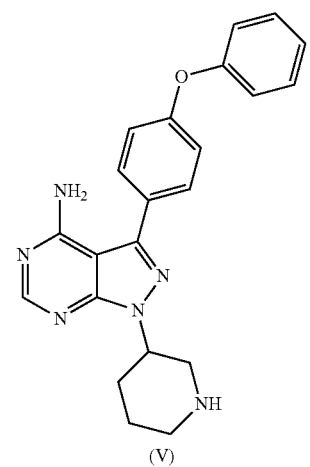

(V)

c) reacting the compound of Formula V with Acrylic acid to yield Ibrutinib

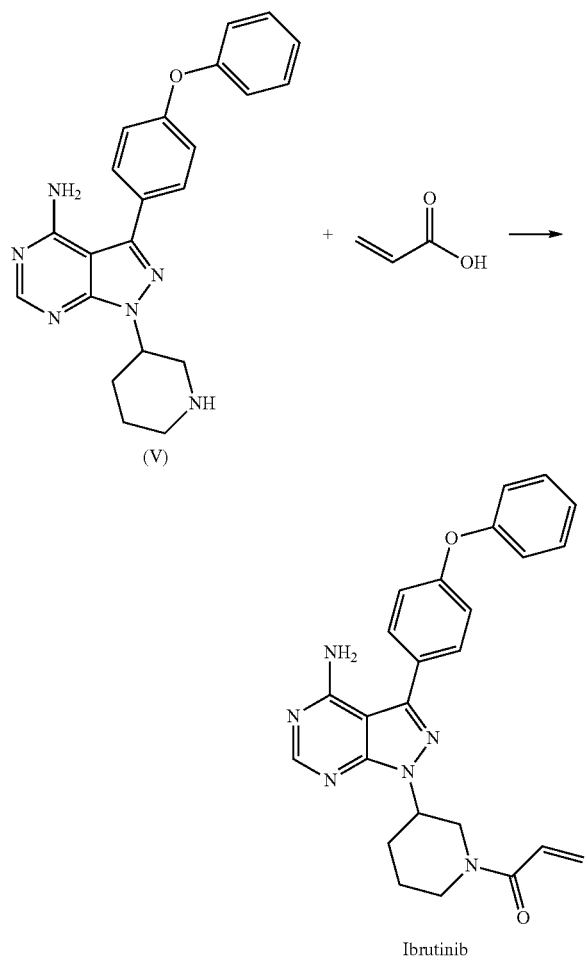

3. A process for the preparation of Ibrutinib (I) according to claim 1, wherein organic solvent used in step a) is performed in presence of a solvent selected from organic solvent is selected from the group consisting of amide solvents formamide, dimethyl formamide, N-methyl-2-pyrrolidone, N-methyl formamide, N-vinyl acetamide, N-vinyl pyrrolidone, 2-pyrrolidone; or alcohols, selected from the group consisting of C2-C6 alcohols like ethanol, 1-propanol, 2-propanol (isopropyl alcohol), 1-butanol, 2-butanol, t-butyl alcohol; or nitriles selected from the group consisting of, acetonitrile or propionitrile; sulfoxides selected from the group consisting of dimethylsulfoxide; halogenated hydrocarbons selected from the group consisting of dichloromethane; aromatic hydrocarbons selected from the group the group consisting of toluene, xylene; esters selected from the group consisting of ethyl acetate, n-propyl acetate, n-butyl acetate, isopropyl acetate, isobutyl acetate, t-butyl acetate; ethers selected from the group consisting of diethyl ether, diisopropyl ether, methyl t-butyl ether, tetrahydrofuran, 1,4-dioxane, 2-methoxyethanol, anisole; ketones selected from the group consisting of acetone, ethyl methyl ketone, diethyl ketone, methyl isobutyl ketone; organic solvents selected from the group consisting of dimethyl formamide, n-hexane, n-heptane, cyclohexane, cycloheptane; hetero aromatic solvents selected from the group consisting of pyridine, dimethyl amino pyridine; water or mixtures thereof.

4. A process for the preparation of Ibrutinib (I) according to claim 1, wherein deprotection step b) is carried out in presence of a catalyst selected from, palladium, palladium on carbon, platinum, platinum on carbon, sodium borohydride, potassium borohydride, ammonium formate, Raney nickel, Rh.

5. A process for the preparation of Ibrutinib (I) according to claim 1, wherein step c) is carried out in presence of a coupling reagent selected from 1-Ethyl-3-(3-dimethylaminopropyl)carbodimide (EDCI), DCC, HOBt, HATU, TATU, CDI or in combination thereof.

* * * * *